United States Patent [19]

Kekesy et al.

[11] 4,058,522

[45] * Nov. 15, 1977

[54] STEROIDS EFFECTIVE AGAINST HEAVY-METAL POISONING

[75] Inventors: Tibor Kekesy; Szabolcs Szeberenyi; György Beer; Antal Dudas; György Hajos; Laszlo Szporny; Eva Czajlik, nee Csizer, all of Budapest, Hungary

[73] Assignee: Richter Gedeon Vegyeszeti Gyar Rt., Budapest, Hungary

[*] Notice: The portion of the term of this patent subsequent to Oct. 26, 1993, has been disclaimed.

[21] Appl. No.: 705,815

[22] Filed: July 16, 1976

Related U.S. Application Data

[63] Continuation-in-part of Ser. No. 481,466, June 20, 1974, Pat. No. 3,988,322.

[30] Foreign Application Priority Data

July 9, 1973 Hungary ............................... RI 514

[51] Int. Cl.$^2$ ............................................. C07J 71/00
[52] U.S. Cl. ............................................. 260/239.57
[58] Field of Search ................................ 260/239.57

[56] References Cited

U.S. PATENT DOCUMENTS 3,897,417 7/1975 Warnant et al. ................ 260/239.57
3,988,322 10/1976 Kekesy et al. ................... 260/239.57

Primary Examiner—Elbert L. Roberts
Attorney, Agent, or Firm—Karl F. Ross

[57] ABSTRACT

A compound of the following formula:

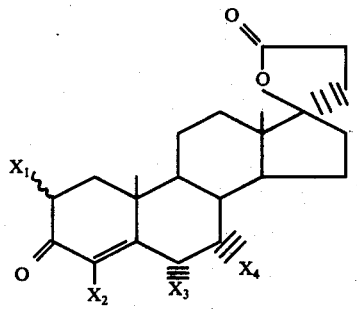

wherein
 $X_1$ is hydrogen or mercapto;
 $X_2$ is mercapto or acetylthio;
 $X_3$ is hydrogen or acetylthio; and
 $X_4$ is hydrogen, acetylthio or $X_3$ and $X_4$ together form a valence bond, but if $X_3$ and $X_4$ form a valence bond $X_2$ is mercapto. The compounds are useful in the treatment of heavy-metal poisoning.

6 Claims, No Drawings

STEROIDS EFFECTIVE AGAINST HEAVY-METAL POISONING

CROSS-REFERENCE TO RELATED APPLICATIONS

This application is a continuation-in-part of U.S. application Ser. No. 481,466 filed 20 June 1974 now U.S. Pat. No. 3,988,322.

This invention relates to pharmaceutically active steriods corresponding to the formula (I), containing acetylthio and/or mercapto groups.

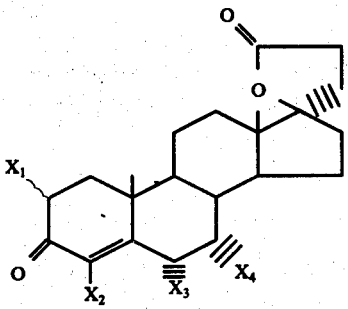

As is known, the derivatives of androst-4-en-17α-(2'-carboxyethyl)-17β-ol-3-one-lactones that contain an acethylthio group in the 7α or 1α and 7α position and a double bond in the 6 position (see J. Org. Chem. 24, 1109, (1959); U.S. Pat. No. 3,013,012) and the corresponding 7α-mercapto compound (see U.S. Pat. No. 3,715,349) possess antialdosteronediuretic activity. Some other publications (see Science 169, 775, (1970); Arzneimittel- Forsch. 21, No. 6, 815 (1971); Steriods 20 (1), 41 (1972) report on the detoxicant effect for mercury poisoning of certain 7α-acetylthio, 7α-mercapto and 1α,7α-diacetylthio steriods belonging to the androstane series. In Chem. Ber. 96 (10), 2803 (1963) the 4-acetylthio and 4-mercapto-testosterone derivatives of anabolic activity, and in Chem. Pharm. Bull. 12 (12), 1433 (1964) the preparation of 6α-acetylthio derivatives of androstane and pregnane compounds containing 4-en-3-keto group, with anti-oestrogen and conadotropic inhibiting effects, are described.

Mercurial poisoning, because of environmental and industrial nocuous effects, has an increasing hygienical importance. Recently, 2,3-dimercapto-1-propanol (The Merck Index, 8th Ed. 372 (1968) has been deemed to be the most suitable agent for therapeutic treatment of mercury poisoning, and almost exclusively this compound is used in therapy in spite of the fact that its administration requires special care. This compound is toxic and cannot be administered orally, but only in the form of an oily intramuscular injection.

The pharmacological behavior of the compounds of the formula (I) has been investigated primarily as to three aspects that are the most characteristic regarding the symptoms of mercurial poisoning. The tests and their results are presented below.

1. Prevention of acute lethal mercurial poisoning:

3.5 mg./kg. of HgCl$_2$ were introduced into Wistar rats, causing a complete mortality (100%). The compounds of the formula (I) decrease the poisoning effect of HgCl$_2$ to a great extent; thus, for example, when administering an oral dosage of 100 mg./kg. body weight of 4-mercapto-androst-4,6-dien-17α-(2'-carboxyethyl)-17β-ol-3-one-lactone, no death occurs upon the introduction of HgCl$_2$ in a dosage of 3.5 mg./kg.; thus complete protection can be achieved. Even the least active of the compounds tested exhibited a protection of 48% in this test.

2. Prevention of renal disorders characteristic of mercurial poisoning.

Nephrocalcinosis:

The intravenous administration of 3.5 mg./kg. of HgCl$_2$ provokes macroscopic nephrocalcinosis (90%). When the animals are treated with the compounds of the formula (I), the occurrence and the extent of nephrocalcinosis drops to zero.

Effect on nephroedema caused by mercurial poisoning:

This effect can be evaluated by determining the water content of the renal tissues. The intravenous administration of 2.0 mg./kg. of HgCl$_2$ causes a pathological increase in the water content by 42 to 54%. The compounds of the formula (I) exert a protecting effect to different extents upon the kidneys of the poisoned animals. The most active compound in this test, 6α-acetylthio-androst-4-en-17α-(2'-carboxyethyl)-17β-ol-3-one-lactone, has a protecting effect of 71%, but even the least active derivative, 4-mercapto-7α-acetylthio-androst-4-en-17α-(2'-carboxyethyl)-17β-ol-3-one-lactone, has a protecting effect of 32%.

Acceleration of the mercury excretion:

Mercury is excreted predominantly in the bile and in the faeces. The compounds tested modify the distribution of mercury in the organism, and increase the amount of mercury excreted in the bile. In this test 4-acetylthio-androst-4,6-dien-17α-(2'-carboxyethyl)-17β-ol-3-one-lactone proved to be the most active; this compound increased the amount of mercury excreted with the bile by 376% under a given test period. Even the less active derivative, 2ξ,4-dimercapto-androst-4,6-dien-17α-(2'-carboxyethyl)-17β-ol-3-one-lactone increased the amount of excreted mercury by 273%.

3. Other pharmacological data:

Upon poisoning with HgCl$_2$, the detoxification activity of the liver exerted on foreign compounds decreases to a great extent. The compounds of the formula (I) prevent the liver-damaging effect of Hg(II) ions. A protecting effect of 70 to 85% can be observed in tests on the hexobarbital oxidase activity under in vivo conditions.

The compounds of the formula (I) show no toxic side-effects in the dosages introduced. The anti-aldosterone activity detectable for many of the compounds does not limit their application to prevent or treat mercurial poisoning, since these compounds do not cause any harmful symptoms under normal aldosterone metabolism.

The pharmacological examination of the compounds of the formula (I) for protection against mercurial poisoning was motivated by the fact that in our opinion mercurial poisoning is the most important problem of public health. As determined from various examinations carried out in our laboratory on animals poisoned with other heavy metals, the compounds in question can also be used to great advantage in preventing saturnine or arsenical poisoning.

Accordingly, this invention relates to pharmaceutically active new steroids corresponding to the formula (I)

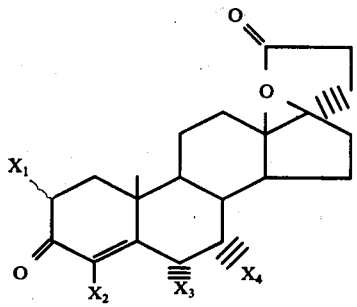

(I)

wherein $X_1$ is hydrogen or mercapto;
$X_2$ is mercapto or acetylthio;
$X_3$ is hydrogen or acetylthio and
$X_4$ is hydrogen, acetylthio or $X_3$ and $X_4$ together form a valence bond but if $X_3$ and $X_4$ form a valence bond $X_2$ is mercapto.

A preferred feature of the invention involves the case wherein $X_1$ is hydrogen is mercapto, $X_2$ or mercapto or acetylthio, $X_3$ is hydrogen, and $X_4$ is hydrogen, acetylthio or $X_3$ and $X_4$ together form a valence bond but if $X_3$ and $X_4$ together form a valence bond, $X_2$ is mercapto.

Another preferred feature of the invention involves the case wherein $X_1$ is mercapto, $X_2$ is mercapto, and $X_3$ and $X_4$ together form a valence bond.

Another preferred feature of the invention involves the case wherein $X_1$ is hydrogen, $X_2$ is mercapto, and $X_3$ and $X_4$ together form a valence bond.

Another preferred feature of the invention involves the case wherein $X_1$ is hydrogen, $X_2$ is acetylthio, $X_3$ is hydrogen, and $X_4$ is acetylthio.

Another preferred feature of the invention involves the case wherein $X_1$ is hydrogen, $X_2$ is mercapto, $X_3$ is hydrogen, and $X_4$ is acetylthio.

The following subgeneric combinations in formula (I) have proved to be advantageous.

| $X_1$ | $X_2$ | $X_3$ | $X_4$ |
|---|---|---|---|
| H | —SH | —SCOCH$_3$ H | —SCOCH$_3$ H |
|   |   | valence bond. |   |
| H | —SCOCH$_3$ | —SCOCH$_3$ H | —SCOCH$_3$ H |
|   |   | valence bond |   |
| $X_1$ | $X_2$ | $X_3$ | $X_4$ |
| —SH | —SCOCH$_3$ | —SCOCH$_3$ H | —SCOCH$_3$ H |
|   |   | valence bond |   |
| —SH | —SH | —SCOCH$_3$ H | —SCOCH$_3$ H |
|   |   | valence bond |   |
| —SH | —SH | —SCOCH$_3$ | H |
| H | —SH | —SCOCH$_3$ | H |
| —SH | —SCOCH$_3$ | —SCOCH$_3$ | H |
| H | —SCOCH$_3$ | —SCOCH$_3$ | H |
| —SH | —SH | H | —SCOCH$_3$ |
| H | —SH | H | —SCOCH$_3$ |
| —SH | —SCOCH$_3$ | H | —SCOCH$_3$ |
| —H | —SCOCH$_3$ | H | —SCOCH$_3$ |
| —SH | —SH | valence bond |   |
| H | —SH | valence bond |   |
| —SH | —SCOCH$_3$ | valence bond |   |
| H | —SCOCH$_3$ | valence bond |   |

The compounds of the formula (I) can be prepared according to the invention as follows: a compound of the formula (III)

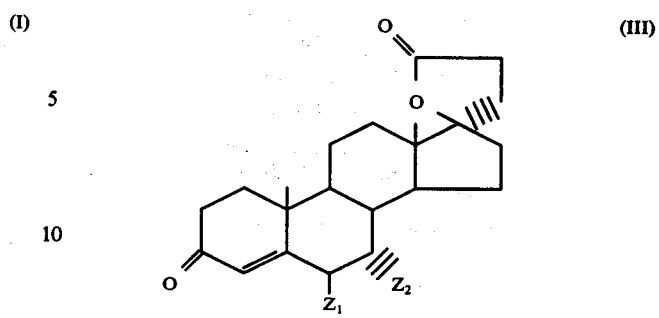

(III)

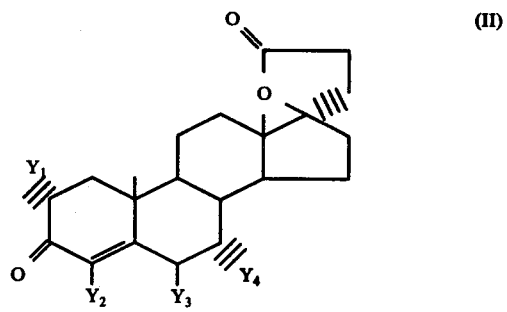

(II)

wherein $Z_1$ is hydrogen and $Z_2$ is hydrogen or acetylthio or $Z_1$ and $Z_2$ form together a valence bond, is brominated, and the thus-obtained compound of the formula (II)

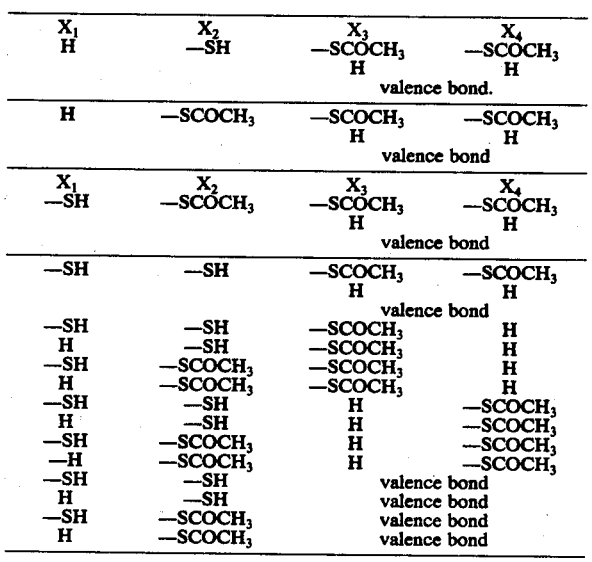

wherein $Y_1$ and $Y_2$ each is hydrogen or bromine, $Y_3$ is bromine, $Y_4$ is hydrogen or acetylthio, or $Y_3$ and $Y_4$ form together a valence bond, is reacted with an alkali metal thioacetate, (e.g. with potassium thioacetate) or with an alkali metal hydrosulphide. A thioacetic acid can be coupled onto the obtained product or the obtained thioacetyl compound can be subjected to alcoholysis.

The compounds of the formula (III) used as starting substances in the process of the invention are known (see J. Org. Chem. 24, 1109 (1959), whereas the intermediates of the formula (II), with the exception of 6β-bromo-androst-4-en-17α-(2'-carboxyethyl)-17β-ol-3-one-lactone, are new compounds.

The intermediates and the end-products can be prepared, according to the invention, in part by known procedures and in part by new methods.

The compounds of formula (II) can be prepared according to the invention by the following bromination methods:

a. Androst-4-en-17α-(2'-carboxyethyl)-17β-ol-3-one-lactone is reacted with N-bromo-succinimide in the presence of carbon tetrachloride to yield 6β-bromo-androst-4-en-17α-(2'-carboxyethyl)-17α-ol-3-one-lactone (see U.S. Pat. No. 3,036,069.

b. Androst-4,6-dien-17α-(2'-carboxyethyl)-17β-ol-3-one-lactone is reacted with N-bromo-succinimide in the presence of perchloric acid and a solvent or, more preferably, a solvent mixture, such as dioxane and water, or this compound is reacted below room temperature with bromine dissolved in a mixture of dioxane and ether or, more preferably, in glacial acetic acid, and the obtained substance is treated with pyridine at elevated temperatures (Chem. Ber. 94, 1225 (1961) to yield the new compound, 4-bromo-androst-4,6-dien-17α-(2'-carboxyethyl)17β-ol-3-one-lactone.

c. Androst-4-en-7α-acetylthio-17α-(2'-carboxyethyl)-17β-ol-3-one-lactone is reacted with 2 molar equivalents of bromine dissolved in glacial acetic acid in the presence of hydrogen bromide and a solvent, preferably in a suspension formed with ether (J.A.C.S. 72, 4534 (1950), or this compound is reacted with bromine in a dioxane solution to form the new substance, 2α,6β-dibromo-7α-acetylthio-androst-4-en-17α-(2'-carboxyethyl)-17β-ol-3-one-lactone.

The new compounds of the formula (I) can be prepared according to the invention as follows:

a. The acetylthio derivatives can be prepared either by reacting the appropriate brominated derivative with potassium thioacetate in the presence of a solvent, preferably a dipolar aprotic solvent such as dimethylformamide, at room temperature (Chem. Pharm. Bull. 12 (12), 1433 (1964); Chem. Ber. 96, (10) 2803 (1963), or by coupling thioacetic acid onto a compound with a double bond in position 6 and a sulphur-containing substituent. The coupling of thioacetic acid can be carried out in the presence of a large excess of thioacetic acid (see U.S. Pat. No. 3,013,012), or in the presence of a solvent such as methanol or dimethylformamide, using thioacetic acid in slight excess (see Hungarian Patent No. 160,369). This method can be use for preparation of 6α-acetylthio-androst-4-en-17α-(2'-carboxyethyl)-17β-ol-3-one-lactone from the appropriate 6β-bromo derivative, and of 4-acetylthio-androst-4,6-dien-17α-(2'-carboxyethyl)-17β-ol-3-one-lactone from the appropriate 4-bromo compound. When reacting 2α,6β-dibromo-7α-acetylthio-17α-(2'-carboxyethyl)-17β-ol-3-one-lactone with potassium thioacetate, however, surprising and nonforeseen elimination and rearrangement reactions take place simultaneously, and 2ζ,4-diacetylthio-androst-4,6-dien-17α-(2'-carboxyethyl)-17β-ol-3-one-lactone is obtained.

b. When coupling thioacetic acid onto a 4-substituted derivative of androst-4,6-dien-17α-(2'-carboxyethyl)-17β-ol-3-one-lactone, 4,7α-diacetylthio-androst-4-en-17α-(2'-carboxyethyl)-17β-ol-3-one-lactone is obtained. Since the coupling of thioacetic acid onto the 4-acetylthio derivative takes place with a very low yield, the above compound is prepared from the appropriate 4-mercapto derivative, according to an advantageous method of the invention. In this reaction, apart from the coupling of thioacetic acid onto the double bond in position 6, surprisingly the acylation of the 4-mercapto group also takes place, and thus the desired compound can be prepared with good yields in a fast reaction.

c. The mercapto derivatives can be prepared by reacting the appropriate bromo compounds with sodium hydrosulphide. This substitution reaction is carried out preferably in the presence of a solvent such as anhydrous tetrahydrofuran, at elevated temperatures, preferably at the boiling point of the system. According to another method, the mercapto compound can be prepared from the appropriate acetylthio derivatives via alcoholysis. This reaction is carried out preferably in an alcohol, such as anhydrous methanol, in the presence of an alkali metal alcoholate, preferably at room temperature (see Chem. Ber. 96 (10), 2803 (1963); U.S. Pat. No. 3,154,542). According to these processes, 4-mercapto-androst-4,6-dien-17α-(2'-carboxyethyl)-17β-ol-3-one-lactone can be prepared from the appropriate 4-bromo or 4-acetylthio compound, or 2ζ,4-dimercapto-androst-4,6-dien-17α-(2'-carboxyethyl)-17β-ol-3-one-lactone can be prepared from the appropriate 2ζ,4-dithioacetyl derivative. When subjecting the 4,7α-diacetylthio-androst-4-en-17α-(2'-carboxyethyl)-17β-ol-3-one-lactone to alcoholysis in methanol in the presence of sodium methoxide as described above, one of the acetylthio groups splits off, while the other is converted into a mercapto group, and thus the starting 4-mercapto-4,6-dien-3-keto compound is obtained. If during this reaction hydrogen sulphide is introduced into the reaction mixture, or the reaction is conducted in methanol in the presence of sodium hydrosulphide, only one of the two acetylthio groups is converted selectively into a mercapto group, and thus 4-mercapto-7α-acetylthio-androst-4-en-17α-(2'-carboxyethyl)-17β-ol-3-one-lactone is obtained.

The new compounds according to the invention can be converted into pharmaceutical products by admixing them with carriers and/or diluents usable in the pharmaceutical industry. The carriers or diluents must be pharmaceutically acceptable organic or inorganic substances that are inert towards the active agents and suitable for enteral or parenteral administration.

The pharmaceutical products may contain the new compounds of the formula (I) either alone or in combination with other known pharmaceutically active agent(s).

If desired, the pharmaceutical compositions can be sterilized or admixed with other auxiliary substances, such as salts influencing the osmotic pressure, buffers, etc.

The invention is elucidated in detail by the aid of the following Examples.

EXAMPLE 1

3.40 g. of androst-4,6-dien-17α-(2'-carboxyethyl)-17β-ol-3-one-lactone are dissolved in a mixture of 28 ml. of dioxane and 42 ml. of ether. The solution is cooled to 10° C., and a solution of 1.70 g. of bromine in 9 ml. of glacial acetic acid is added within 2 minutes. The ether is evaporated from the reaction mixture in vacuo and the residual dioxane solution is poured into 250 ml. of water. The separated substance is filtered off, the wet solid is dissolved in 80 ml. of pyridine, and the solution is refluxed for one hour. Thereafter the reaction mixture is cooled, poured into 500 ml. of water containing 10% hydrochloric acid, the separated product is filtered off and recrystallized from methanol. 1.80 g. (43%) of 4-bromo-androst-4,6-dien-17α-(2'-carboxyethyl)-17β-ol-3-one-lactone are obtained; m.p.: 193-194° C.; $(\alpha)_D^{20} = +101°$ (c = 1, in chloroform); $\lambda_{max}$: 302 nm ($\Sigma_M = 22,000$); $\nu_{max}$ 1780, 1670, 1615, 1550 cm$^{-1}$.

EXAMPLE 2

4.16 g. of 7α-acetylthio-androst-4-en-17α-(2'-carboxyethyl)-17β-ol-3-one-lactone are dissolved in 160 ml. of dioxane, then a solution of 3.36 g. of bromine in 80 ml. of dioxane is added to the mixture at room temperature, within 20 minutes. The reaction mixture is stirred further for 20 minutes and poured onto 2 l. of water. The separated product is filtered off, washed until neutral, suctioned and suspended in methanol. The solids are filtered off again, dried and recrystallized from acetone. 4.20 g. (73%) of 2α,6β-dibromo-7α-acetylthio-androst-4-en-17α-(2'-carboxyethyl)-17β-ol-3-one-lactone are obtained; m.p.: 186°-187° C.; $(\alpha)_D^{20} = +7.2°$ (c = 1, in chloroform); $\lambda_{max}$ 254 nm ($\Sigma_M = 14,200$); $\nu_{max}$ 1775, 1700, 1685, 1612 cm$^{-1}$.

EXAMPLE 3

4.21 g. of 6β-bromo-androst-4-en-17α-(2'-carboxyethyl)-17β-ol-3-one-lactone are dissolved in 62 ml. of dimethylformamide, and 3.4 g. of potassium thioacetate are added to the stirred solution at room temperature. The reaction mixture is stirred for an additional 3 hours, thereafter poured onto 300 ml. of water. The separated precipitate is filtered off, washed until neutral, and dried. The obtained crude product is recrystallized from methanol to yield 3.00 g. (72%) of 6α-acetylthio-androst-4-en-17α-(2'-carboxyethyl)-17β-ol-3-one-lactone; m.p.: 194°–196° C; $(\alpha)_D^{20} = +37°$ (c = 1, in chloroform); $\lambda_{max.}$ 236 nm $(\Sigma_M = 15,900)$; $\nu_{max.}$ 1770, 1675, 1620 cm$^{-1}$.

EXAMPLE 4

4.19 g. of 4-bromo-androst-4,6-dien-17α-(2'-carboxyethyl)-17β-ol-3-one-lactone are dissolved in 50 ml. of dimethyl formamide, and 2.8 g. of potassium thioacetate are added to the stirred solution at room temperature. The reaction mixture is stirred for an additional 10 hours, thereafter it is poured onto 300 ml. of water. The separated precipitate is filtered off, washed with water, suctioned, and the wet substance is recrystallized from acetone. 2.5 g. (61%) of 4-acetylthio-androst-4,6-dien-17α-(2'-carboxyethyl)-17β-ol-3-one-lactone are obtained; m.p.: 230°–233° C.; $(\alpha)_D^{20} = +52.5°$ (c = 1, in chloroform) $\lambda_{max.}$ 300 nm $(\Sigma_M = 18,600)$; $\nu_{max.}$ 1780, 1705, 1670, 1610, 1545 cm$^{-1}$.

EXAMPLE 5

4.19 g. of 4-bromo-androst-4,6-dien-17α-(2'-carboxyethyl)-17β-ol-3-one-lactone are dissolved in 50 ml. of anhydrous tetrahydrofuran under nitrogen atmosphere, with the exclusion of moisture. 5.6 g. of sodium hydrosulphide are added to the solution, and the mixture is refluxed for 5 hours. The reaction mixture is cooled, adjusted to pH 6 with glacial acetic acid, and poured onto 400 ml. of water. The separated product is filtered off, washed, the wet substance is suspended in methanol, filtered again, and dried. 2.20 g. (59%) of 4-mercapto-androst-4,6-dien-17α-(2'-carboxyethyl)-17β-ol-3-one-lactone are obtained; m.p.: 180-185° C.; $(\alpha)_D^{20} = +140.8°$ (c = 1, in chloroform); $\lambda_{max.}$ 338 nm $(\Sigma_M = 11,700)$; $\nu_{max.}$ 2545, 1775, 1660, 1612, 1545 cm$^{-1}$.

EXAMPLE 6

0.46 g. of metallic sodium are dissolved in 170 ml. of anhydrous methanol under nitrogen atmosphere, with the exclusion of moisture, thereafter 4.14 g. of 4-acetylthio-androst-4,6-dien-17α-(2'-carboxyethyl)-17β-ol-3-one-lactone are added to the stirred solution. When the solids are dissolved, the mixture is stirred for an additional 30 minutes at room temperature, thereafter the pH of the mixture is adjusted to 6 with glacial acetic acid. The mixture is evaporated to about 1/5 of the original volume under nitrogen atmosphere. The separated crystals are filtered off, washed with cold methanol and dried. 2.50 g. (67%) of 4-mercapto-androst-4,6-dien-17α-(2'-carboxyethyl)-17β-ol-3-one-lactone are obtained; m.p.: 188-192° C., $(\alpha)_D^{20} = +146.8°$ (c = 1, in chloroform); $\lambda_{max.}$ 338 nm $(\Sigma_M = 11,900)$; $\nu_{max.}$ 2545, 1775, 1660, 1612, 1645 cm$^{-1}$.

EXAMPLE 7

5.74 g. of 2α,6β-dibromo-7α-acetylthio-androst-4-en-17α-(2'-carboxyethyl)-17β-ol-3-one-lactone are dissolved in 90 ml. of dimethylformamide, and 4.56 g. of potassium thioacetate are added to the stirred solution at room temperature. The reaction mixture is stirred for an additional 2 hours, thereafter it is poured into 400 ml. of water and extracted with 3×100 ml. of methylene chloride. The organic extracts are collected, dried over anhydrous sodium sulphate, filtered and evaporated to dryness. The obtained product is recrystallized from ethanol. 4.00 g. (82%) of 2 Σ,4-diacetylthio-androst-4,6-dien-17α-(2'-carboxyethyl)-17β-ol-3-one-lactone are obtained; m.p.: 160°–170° C; $\lambda_{max.}$ 231, 301 nm $(\Sigma_M = 14,700, 11,900)$; $\nu_{max.}$ 1775, 1705, 1680, 1610, 1545 cm$^{-1}$.

EXAMPLE 8

0.92 g. of metallic sodium are dissolved in 240 ml. of anhydrous methanol under nitrogen atmosphere with the exclusion of moisture, than 4.88 g. of 2ζ,4-diacetylthio-androst-4,6-dien-17α-(2'-carboxyethyl)-17β-ol-3-one-lactone are added to the stirred solution at room temperature. When the solids are dissolved, the mixture is stirred for additional 5 minutes, thereafter the pH of the mixture is adjusted to 6 with glacial acetic acid. The solution is evaporated to 1/4$^{th}$ of the original volume under a nitrogen atmosphere. The separated product is filtered of, washed with methanol and dried. 2.95 g. (73%) of 2 ζ,4-dimercapto-androst-4,6-dien-17α-(2'-carboxyethyl)-17β-ol-3-one-lactone are obtained; m.p.: 233°–240° C.; $\lambda_{max.}$ 337 nm $(\Sigma_M = 6,200)$; $\nu_{max.}$ 2250, 1775, 1660, 1610, 1545 cm$^{-1}$.

EXAMPLE 9

3.72 g. of 4-mercapto-androst-4,6-dien-17α-(2'-carboxyethyl)-17β-ol-3-one-lactone are dissolved in 20 ml. of thioacetic acid, and the solution is refluxed for 1.5 hours. The excess of thioacetic acid is distilled off in vacuo, and the obtained oily residue is recrystallized from ethanol. 3.00 g. (61%) of 4,7α-diacetylthio-androst-4-en-17α-(2'-carboxyethyl)-17β-ol-3-one-lactone are obtained; m.p.: 186°–194° C.; $(\alpha)_D^{20} = +72.8°$ (c = 1, in chloroform); $\lambda_{max.}$ 234 nm $(\Sigma_M = 14,100)$; $\nu_{max.}$ 1775, 1705, 1685, 1575 cm$^{-1}$.

EXAMPLE 10

0.46 g. of metallic sodium are dissolved in 250 ml. of anhydrous methanol under the exclusion of moisture, then gaseous hydrogen sulphide is introduced into the solution at room temperature for 15 minutes. 4.90 g. of 4,7α-(dithioacetyl-androst-4-en-17α-(2'-carboxyethyl)-17β-ol-3-one-lactone are added to the solution saturated with hydrogen sulphide, and the reaction mixture is stirred at room temperature under further introduction of hydrogen sulphide. Thereafter the pH of the solution is adjusted to 6 with glacial acetic acid, and the mixture is evaporated to dryness. The crude product is washed with water, dried, and recrystallized from isopropanol. 2.45 g. (55%) of 4-mercapto-7α-acetylthio-androst-4-en-17α-(2'-carboxyethyl)-17β-ol-3-one-lactone are obtained; m.p.: 186°–188° C; $(\alpha)_D^{20} = +37.2°$ (c = 1, in chloroform); $\lambda_{max.}$ 302 nm $(\Sigma_M = 6.300)$; $\nu_{max.}$ 2550, 1770, 1695, 1680, 1580 cm$^{-1}$.

We claim:

1. A compound of the following formula:

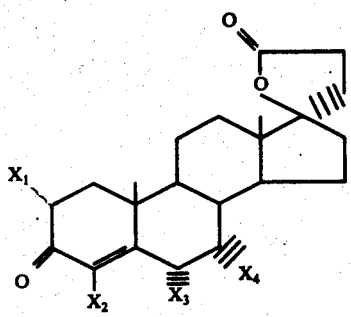

wherein
$X_1$ is hydrogen or mercapto;
$X_2$ is mercapto or acetylthio;
$X_3$ is hydrogen or acetylthio; and
$X_4$ is hydrogen, acetylthio or $X_3$ and $X_4$ together form a valence bond, but if $X_3$ and $X_4$ form a valence bond $X_2$ is mercapto.

2. The compound defined in claim wherein $X_1$ is mercapto, $X_2$ is mercapto and $X_3$ and $X_4$ together form a valence bond.

3. The compound defined in claim 1 wherein $X_1$ is hydrogen, $X_2$ is mercapto and $X_3$ and $X_4$ together form a valence bond.

4. The compound defined in claim 1 wherein $X_1$ is hydrogen, $X_2$ is acetylthio, $X_3$ is hydrogen, and $X_4$ is acetylthio.

5. The compound defined in claim 1 wherein $X_1$ is hydrogen, $X_2$ is mercapto, $X_3$ is hydrogen, and $X_4$ is acetylthio.

6. A method of treating an animal for heavy-metal poisoning comprising administering an effective amount of a compound as defined in claim 1.

* * * * *